United States Patent [19]

Ruoslahti et al.

[11] Patent Number: 5,180,809

[45] Date of Patent: Jan. 19, 1993

[54] ADHESION RECEPTOR FOR LAMININ AND ITS USE

[75] Inventors: Erkki I. Ruoslahti; Eva Engvall, both of Rancho Santa Fe; Kurt R. Gehlsen, San Diego, all of Calif.

[73] Assignee: La Jolla Cancer Research Foundation, La Jolla, Calif.

[21] Appl. No.: 357,354

[22] Filed: May 25, 1989

Related U.S. Application Data

[63] Continuation-in-part of Ser. No. 196,986, May 20, 1988, abandoned.

[51] Int. Cl.$^5$ .................. C07K 15/06; C07K 15/14; C07K 3/20; C07K 17/02
[52] U.S. Cl. .................. 530/350; 530/395; 530/413; 530/810; 530/388.22; 530/389.1; 424/450
[58] Field of Search .............. 436/501, 503, 518, 534, 436/547, 548, 829; 435/7.21, 7.23; 424/420, 450; 530/350, 387, 395, 413, 810; 514/2

[56] References Cited

U.S. PATENT DOCUMENTS 4,565,789  1/1986  Liotta et al. .................. 436/504

OTHER PUBLICATIONS

K. R. Gehlsen et al., Science 241:1228-1229, Sep. 2, 1988.
K. R. Gehlsen et al., Science 245:342-343, Jul. 28, 1989.
Hynes, R. O., Integrins: A Family of Cell Surface Receptors, Cell 48:549-554 (1987).
Pytela et al., Arginine-Glycine-Aspartic Acid Adhesion Receptors, Methods in Enzymology 144:475-489 (1987).
Graf et al., Identification of an Amino Acid Sequence in Laminin Mediating Cell Attachment, Chemotaxis, and Receptor Binding, Cell 48:989-996 (1987).
Wewer et al., Human Laminin Isolated in a Nearly Intact, Biologically Active Form from Placenta by Limited Proteolysis, The Journal of Biological Chemistry 258:12654-12660 (1983).
Wewer et al., Role of Laminin Receptor in Tumor Cell Migration, Biological Abstracts vol. 85 (1988) abstract No. 17879, Cancer Research 47:5691-5698 (1987).
Gregoriadis, G. and Senior, J., Targeting of Small Unilamellar Liposomes to the Galactose Receptor In Vivo, Biochemical Society Transactions 12:337-339 (1984).
Hand et al., Express of Laminin Receptor in Normal and Carcinomatous Human Tissues as Defined by a Monoclonal Antibody, Biological Abstracts vol. 80 (1985) abstract No. 41870, Cancer Research 45:2713-2719 (1985).
Barsky et al., Characterization of a Laminin Receptor From Human Breast Carcinoma Tissue, Breast Cancer Research and Treatment 4:181-188 (1984).
Hemler et al., The VLA Protein Family, Characterization of Five Distinct Cell Surface Heterodimers Each With a Common 130,000 Molecular Weight Beta Subunit, The Journal of Biological Chemistry 262:3300-3309 (1987).
Horwitz et al., The Cell Substrate Attachment (CSAT) Antigen Has Properties of a Receptor for Laminin and Fibronectin, The Journal of Cell Biology 101:2134-2144 (1985).
Lesot et al., Isolation of a Laminin-Binding Protein From Muscle Cell Membranes, The EMBO Journal 2:861-865 (1983).

(List continued on next page.)

Primary Examiner—Robert A. Wax
Assistant Examiner—Stephen Walsh
Attorney, Agent, or Firm—Pretty Schroeder Brueggemann & Clark

[57] ABSTRACT

An adhesion receptor for laminin is provided. The receptor is isolated from cell or tissue extracts and fractionated on an affinity column composed of cell attachment-promoting fragments of laminin coupled to Sepharose TM in the presence of divalent cations. This receptor can be used to prepare specific antibodies for the analysis of the amount of laminin receptor expressed by cells and has other applications in cellular and tumor biology.

8 Claims, 5 Drawing Sheets

OTHER PUBLICATIONS

Herbert L. Malinoff and Max S. Wicha, Isolation of a Cell Surface Receptor Protein for Laminin from Murine Fibrosarcoma Cells, The Journal of Cell Biology 96:1475–1479 (1983).

Michael D. Pierschbacher and Erkki Ruoslahti, Cell Attachment Activity of Fibronectin Can Be Duplicated by Small Synthetic Fragments of the Molecule, Nature 309:30–33 (1984).

Rao et al., Isolation of a Tumor Cell Laminin Receptor, Biochemical and Biophysical Research Communications 111:804–808 (1983).

Neil R. Smalheiser and Nancy B. Schwartz, Cranin: A Laminin-Binding Protein of Cell Membranes, Proc. Natl. Acad. Sci. USA 84:6457–6461 (1987).

Terranova et al., Laminin Receptor on Human Breast Carcinoma Cells, Proc. Natl. Acad. Sci. USA 80:444–448 (1983).

Klaus von der Mark and Uwe Kuhl, Laminin and its Receptor, Biochimica et Biophysica Acta 823:147–160 (1985).

Elizabeth A. Wayner and William G. Carter, Identification of Multiple Cell Adhesion Receptors for Collagen and Fibronectin in Human Fibrosarcoma Cells Possessing Unique Alpha and Common Beta Subunits, The Journal of Cell Biology 105:1873–1884 (1987).

Tomaselli et al., Interactions of a Neuronal Cell Line (PC12) with Laminin, Collagen IV, and Fibronectin: Identification of Integrin-Related Glycoproteins Involved in Attachment and Process Outgrowth, The Journal of Cell Biology 105:2347–2358 (1987).

Takada et al., Fibronectin Receptor Structures in the VLA Family of Heterodimers, Nature 326:607–609 (1987).

Sonnenberg et al., Laminin Receptor on Platelets is the Integrin VLA-6, Nature 336:487–489 (1988).

Takada et al., The Very Late Antigen Family of Heterodimers in Part of a Superfamily of Molecules Involved in Adhesion and Embryogenesis, Proc. Natl. Acad. Sci. USA 84:3239–3243 (1987).

Hall et al., Embryonic Neural Retinal Cell Response to Extracellular Matrix Proteins: Developmental Changes and Effects of the Cell Substratum Attachment Antibody (CSAT), The Journal of Cell Biology 104:623–634 (1987).

Takada et al., Extracellular Matrix Receptors, ECMRII and ECMRI, for Collagen and Fibronectin Correspond to VLA-2 and VLA-3 in the VLA Family of Heterodimers, Journal of Cellular Biochemistry 37:385–393 (1988).

ADHESION RECEPTOR FOR LAMININ AND ITS USE

RELATED APPLICATIONS

This application is a continuation-in-part of U.S. Ser. No. 196,986, filed May 20, 1988, now abandoned.

FIELD OF INVENTION

This invention relates generally to the fields of cell adhesion systems and specifically to an adhesion receptor for laminin.

BACKGROUND OF THE INVENTION

Much of what goes on at the cell surface relates to the recognition by the cell of substances around it. A prime example is the binding of soluble hormones by the cell and its response to such binding. Another important aspect of cell surface recognition is the interaction of the cell with insoluble structures that surround it. Such a structure can be the surface of another cell or the extracellular matrix.

Although the interactions of cells with one another and with extracellular matrices are not well understood, they play an important role in the life of the cell. For example, cell-matrix and cell-cell interactions seem to tell a cell where in the body it is supposed to be or where it is supposed to go if it has to migrate. A particularly intriguing example is nerve cells which send out processes to appropriate positions and thereby form connections to distant parts of the body. Positional signalling is obviously impaired in cancer since tumors invade and disseminate into parts of the body inappropriate for their cell of origin. In fact, as our understanding of the cell-matrix and cell-cell interactions increases and their exploration becomes possible, this field is very likely to develop into a new, important frontier of medicine.

Both proteins and carbohydrates at the cell surface can participate in the cell-matrix and cell-cell interactions. Extracellular matrices are composed of an insoluble meshwork of protein and carbohydrate that is laid down by cells and fills most of the intercellular spaces. Matrices in different locations in the body consist of different combinations of collagens, proteoglycans, elastin, hyaluronic acid and various glycoproteins such as fibronectin and laminin. Virtually all of the extracellular matrix glycoproteins and collagens that have been identified interact with cells.

The most readily observable result of the interaction of cells with the extracellular matrix molecules is cell adhesion. The adhesive properties of the extracellular matrix proteins can be easily demonstrated in vitro by plating cells onto a surface coated with extracellular matrix material or with one of the purified matrix proteins. The cells will rapidly adhere to such a surface and spread on it. However, the adhesive proteins not only promote adhesion, they also stimulate cell migration. When confronted with limiting concentrations of an adhesive protein applied as a gradient on a surface, cells move toward the higher concentration.

More complex ways in which extracellular matrices influence cells are to promote cell differentiation, survival and growth. One of the extracellular matrix proteins, laminin, has particularly striking effects on cells. This protein, which is present in the specialized extracellular matrix sheets, basement membranes, promotes the attachment and migration of cells and plays a role in differentiation and tumor metastasis. Laminin also promotes and guides the growth of nerve cell processes, or neurites.

These interactions between cells and laminin are thought to be mediated by cell surface receptors which function as the adhesion receptor for laminin. The full nature of the receptor, or receptors, that mediate the effects of laminin on cells is still unknown.

There thus exists a need to identify and isolate laminin adhesion receptors. The availability of isolated receptor will allow production of antibodies specific for this receptor, which could be used, for example, to assay for the expression of laminin receptors at the surface of tumor cells. Compounds, such as recombinant protein fragments that bind to the receptor, can be used to reproduce the activity of laminin or to inhibit the adhesion of cells to laminin- containing structures. Moreover, there exists a need to be able to target liposomes to specific tissues for therapeutic or other purposes. The present invention satisfies these needs and provides additional advantages as well.

SUMMARY OF THE INVENTION

The present invention provides a substantially pure mammalian laminin adhesion receptor characterized in that it comprises two subunits, $\alpha$ and $\beta$, and interacts with laminin and cell attachment-promoting fragments of laminin from the portion of laminin that consists of the COOH-terminal portions of its polypeptides. The interaction with laminin or cell-attachment promoting fragments of laminin is divalent-cation dependent. The larger ($\alpha$) subunit is reactive with anti-$\alpha_3$ antisera.

In one aspect, the invention provides a method of isolating and purifying the laminin adhesion receptor. In another aspect of the present invention, monoclonal and polyclonal antibodies are prepared against the isolated receptor and their reactivity is assayed against the purified receptor. Because no other receptors are known to contain $\alpha_3$ subunit, antibodies against the larger alpha subunit are specific to the laminin receptor, whereas some antibodies against the smaller beta subunit can react with the fibronectin receptor and other related cell adhesion receptors. The anti-alpha subunit antibodies are useful in determining the amount of laminin receptor which is expressed by a given cell type. Further selection by cell attachment assays provides anti-alpha subunit antibodies that can inhibit the attachment of cells to laminin. Such antibodies prevent the invasion of tumor cells through amniotic membrane tissue in an in vitro assay.

In another aspect of the invention, the receptor is used to provide compounds that can reproduce or inhibit the function of the laminin receptor. In a further aspect of the present invention, the cell surface receptors are incorporated into the membranes of liposomes. Such liposomes are then used to target the contents of the liposomes to tissues containing laminin.

BRIEF DESCRIPTION OF THE DRAWINGS

FIG. 1. Sodium dodecyl sulfate-polyacrylamide gel electrophoresis (SDS-PAGE) analysis of fractions eluted from the laminin affinity matrix. RuGli glioblastoma cells were surface-labeled and extracted, and the extract fractionated as described in Example I on a Sepharose TM column containing covalently bound, cell-attachmentpromoting fragments of laminin. Aliquots of each fraction were analyzed by SDS-PAGE under nonreducing conditions, using autoradiography for visualization of protein bands. Lanes 1–13 show fractions from the EDTA elution of the column. The molecular weight markers were: myosin, 200 kD; beta-galactosidase, 116 kD; phosphorylase B, 94 kD; bovine serum albumin, 67 kD; ovalbumin, 43 kD.

FIG. 3. Immunoblot analysis of laminin receptor. The fibronectin (A) and laminin (B) receptors isolated from RuGli cells were electrophoresed under nonreducing conditions and transferred to nitrocellulose filters, and the filters were incubated with rabbit anti-fibronectin receptor antibodies (Argraves et al. J. Cell Biol. 105:1183, 1987, which is incorporated herein by reference) followed by detection of the bound antibodies with goat anti-rabbit IgG conjugated to horseradish peroxidase.

FIG. 4. Immunoblot analysis of laminin and fibronectin receptors. The fibronectin (Lanes 1, 3) and laminin (Lanes 2, 4) receptors isolated from RuGli cell extracts were electrophoresed under nonreducing conditions and transferred to nitrocellulose filters. The filters were incubated with either rabbit antiserum against the fibronectin receptor absorbed with Sepharose-coupled laminin receptor (Lanes 1, 2) or with a rabbit anti-laminin receptor antiserum absorbed with Sepharose-coupled fibronectin receptor (Lanes 3, 4). Bound antibodies were detected with goat anti-rabbit IgG conjugated to horseradish peroxidase. The anti-fibronectin receptor antibody used for absorption has been described (Pytela et al., Meth. Enzymol., 144:475-489 (1987), which is incorporated herein by reference), the anti-laminin receptor antiserum was prepared by immunizing with receptor purified from RuGli cells as described in Example I.

FIG. 5. Binding of laminin receptor-containing liposomes to substrates. Microtiter wells were coated with various proteins and unoccupied binding sites on the plastic were blocked by incubating the wells with bovine serum albumin. The binding or inhibition of binding of receptor liposomes to the wells was then tested as described in Example II. The results of six experiments are expressed as a percentage of maximal binding. The mean plus standard error after subtraction of background from BSA attachment is shown: LM, human laminin; FN, fibronectin; IV, type IV collagen; LM+LM fragments, LM+ 20 μg of chymotryptic laminin fragments; LM+RGD, LM+1 mg/ml GRGDSP peptide; LM+YIGSR, LM+1 mg/ml YIGSR peptide; fibronectin receptor liposomes (open bars); LMR, laminin receptor liposomes (shaded bars).

FIG. 6. Radioreceptor binding assay. Purified iodinated laminin receptors isolated from various human (MG-63, A431) and rat (RuGli, NRK-49F) cells were allowed to incubate with various proteins coated onto microtiter wells. The wells were washed and bound receptor was solubilized in 1% SDS in TBS and quantitated in a gamma counter. The results are expressed as a percentage of receptor bound, with laminin binding equal to 100 percent. The bars represent receptors from different cell types as indicated in the Figure-LM, human laminin; FN, human fibronectin; CIV, Type IV collagen; CI, Type I collagen; BSA, bovine serum albumin.

DETAILED DESCRIPTION OF THE INVENTION

The present invention relates to a mammalian adhesion receptor for laminin. Laminin is known to have a role in both the differentiation of normal cells and the metastasis of malignant ones. The isolation of this receptor and antibodies reactive with it can be used to detect the presence of the laminin receptor on the surface of tumor cells. The ability of cells to bind to laminin has been found to correlate with their invasive and metastatic capacity.

To isolate and purify the mammalian laminin adhesion receptor, extracts of surface-labeled mammalian cells were fractionated on immobilized laminin fragments that are capable of promoting cell attachment. Preferably such cells are malignant cells of neural derivation, although other mammalian cell types can be used as well. For example, rat glioblastoma cells (RuGli) were first surface-iodinated with lactoperoxidase and dissolved in octylglucoside. The RuGli cells attach to and spread on a plastic surface coated laminin. Addition of $Mn^{2+}$ to the cell suspension during attachment assay enhances the attachment of the cells to the laminin-coated surface. By applying the same purification method, a receptor can be isolated from other cell types and tissues, such as human osteosarcoma MG-63 cells or placental tissues.

Figure 1:
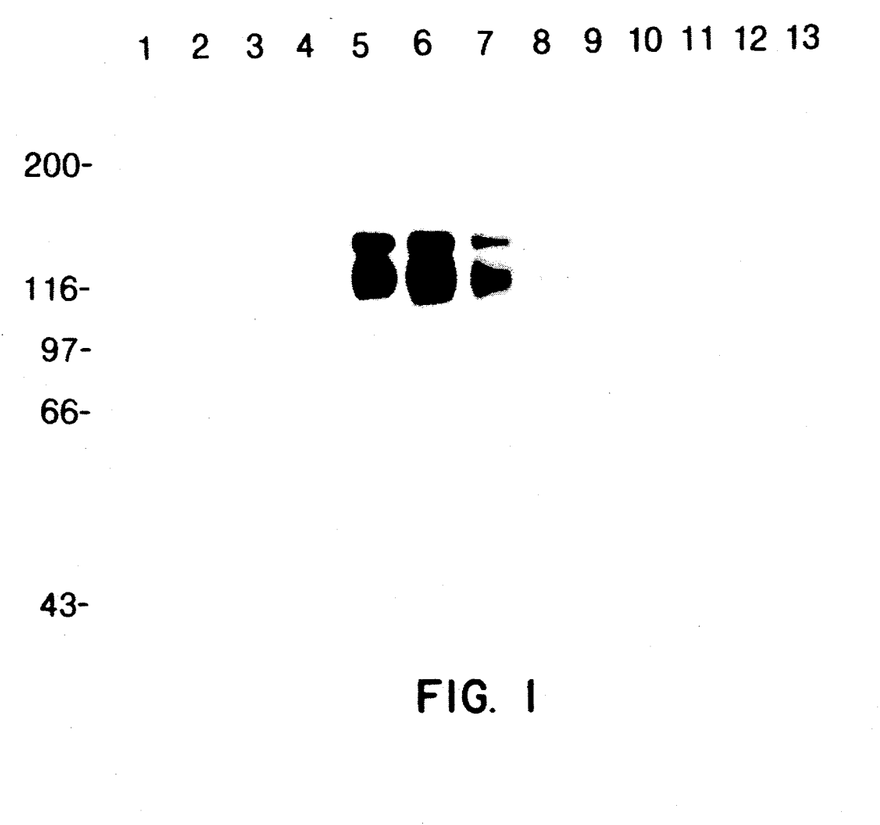
Figure 2:
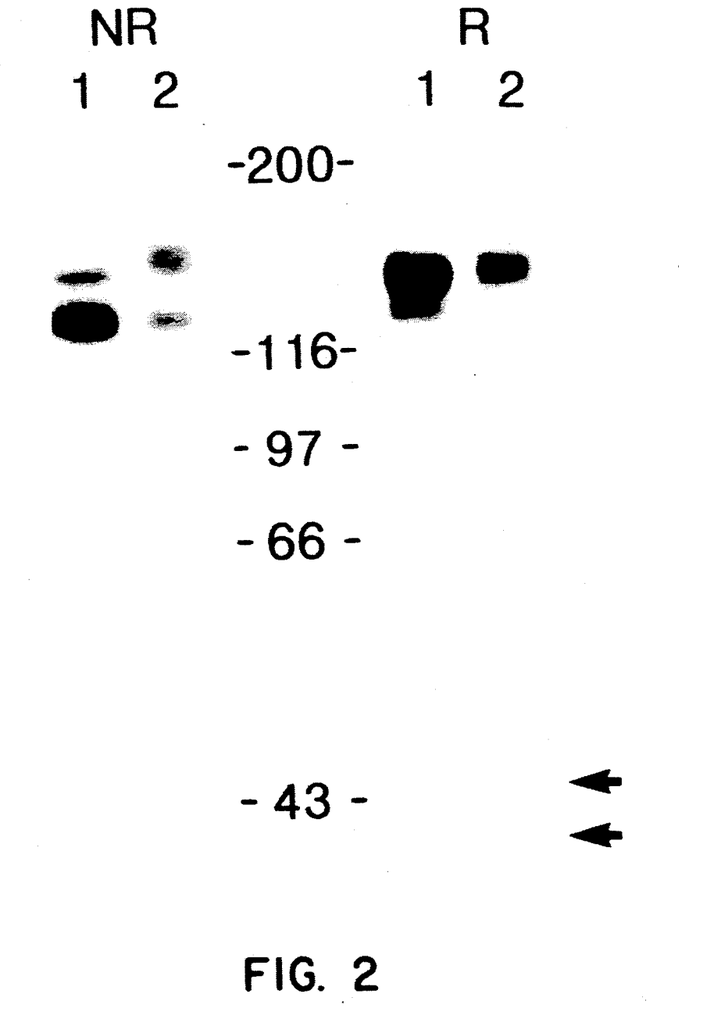
FIG. 2. SDS-PAGE analysis of the RuGli laminin receptor (lane 1) and the fibronectin receptor (lane 2) under nonreducing (NR) and reducing (R) conditions. The fibronectin receptor was obtained from the same cell extract as the laminin receptor by using fibronectin cell attachment fragment-Sepharose ™ as the affinity matrix using the method of Pytela et al. Cell 40:548, (1985), which is incorporated herein by reference. The conditions of the electrophoresis were the same as in FIG. 1. Arrows indicate the light chains of the alpha subunits.

Laminin fragments maintaining cell-attachment promoting activity were isolated generally by the method of Engvall et al., J. Cell Biol. 103:2457 (1986), which is incorporated herein by reference. Various modifications can be made to this method, including the use of intact laminin or fragments generated with proteases other than pepsin and chymotrypsin. An affinity matrix was prepared by coupling the laminin fragments to cyanogen-bromide (CNBr)-activated Sepharose ™ (Sigma, St. Louis, Mo.). Specific elution was effected by treating the column with EDTA (ethylene diaminotetraacetic acid). All buffers, except the elution buffer, contained 1 mM $Mn^{2+}$ to facilitate the binding of the receptor to the affinity matrix. The eluted fractions were analyzed by SDS-PAGE followed by autoradiography. As shown in FIGS. 1 and 2, in the incompletely unfolded state in which the protein derived from RuGli cells exists under non-reducing conditions, two protein bands migrating at positions corresponding to the apparent molecular weights of 150 kD and 120 kD were seen.

A more accurate molecular weight determined by SDS-PAGE under reducing conditions indicates the molecular weights of these subunits are about 165 and 140 kD, respectively, because, when reduced, the larger of the subunits gives rise to two polypeptides, having molecular weights of 135 kD and 35 kD. The smaller component appears as a 35/30 kD doublet in this analysis. While not wishing to be bound by this explanation, it is believed that the 30 kD polypeptide is a cleavage fragment of the 35 kD polypeptide.

A laminin binding protein with subunits similar to those of the RuGli cell protein was also isolated from human MG-63 osteosarcoma cells and placental tissues. This human laminin receptor is also composed of two polypeptides. However, the larger subunit has a native molecular weight of 170,000 D.

As used herein, the term "laminin adhesion receptor" (also termed "adhesion receptor for laminin") refers to a cell surface receptor which functions in mediating the adhesion of cells to laminin. It selectively binds to laminin or laminin fragments that retain cell attachment promoting activity and does not bind substantially to vitronectin, fibrinogen, collagen type I or albumin. The native laminin adhesion receptor is composed of two subunits having molecular weights of about 165 to 170 kD and about 140 kD. The larger polypeptide in turn is composed of two disulfide linked chains with molecular weights of about 135 kD and 35 kD.

The term "laminin adhesion receptor" refers to both the native structures and modifications or isoforms of those structures which retain laminin or laminin-fragment binding activity. Laminin or laminin-fragments retaining cell attachment promoting activity are referred to as the ligand of the laminin adhesion receptor. It is understood that limited modifications may be made to the structure of the laminin adhesion receptor without destroying the ligand binding activity and that only a portion of the entire primary structure may be required in order to effect activity. Fragments of the receptor that retain the ligand binding activity are included within the definition.

"Substantially pure," when used to describe the state of the laminin adhesion receptor of the invention, denotes the receptor essentially free of other proteins normally associated with or occurring with the receptor in its native environment and substantially separated from interfering and diluting cell surface proteins or other proteins, such as antibodies, introduced through, for example, isolation procedures. More than one isoform of the receptor may be present, however, in the "substantially pure" preparation.

The heterodimeric structure of the isolated laminin adhesion receptor, the disulfide-bonded two-chain composition of its larger subunit and the increase in molecular weight of the smaller subunit upon reduction are all characteristic of the class of receptors termed integrins (See Ruoslahti and Pierschbacher, Science 238:491 (1987), which is incorporated herein by reference). Integrins, which include a number of receptors, share amino acid sequence similarities.

Figure 3:
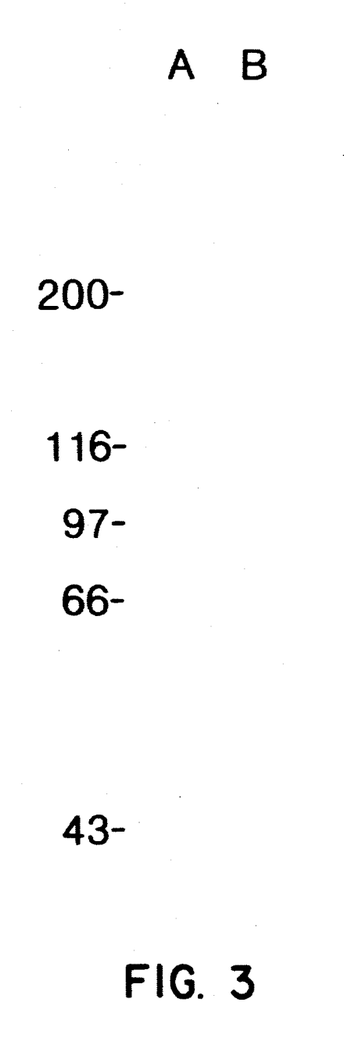
Figure 4:
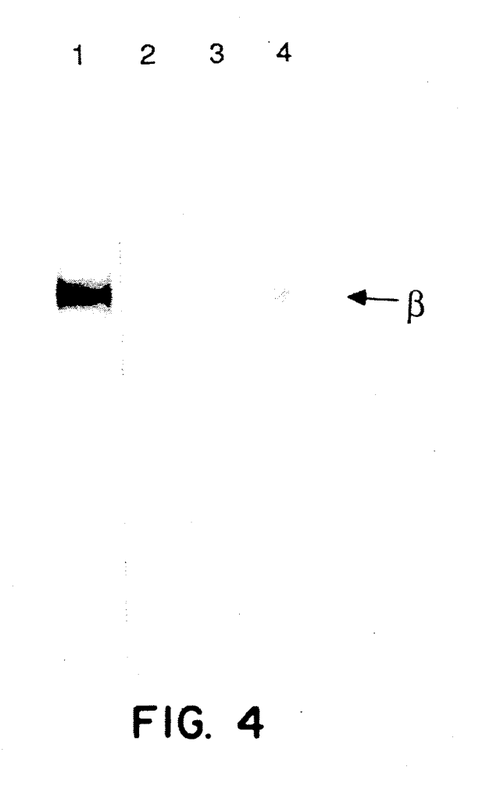

To explore the relationship of the laminin adhesion receptor with known integrins, the receptor was immunoblotted with affinity-purified polyclonal antibodies to the fibronectin and vitronectin receptors. The antifibronectin receptor antibody cross-reacted with the smaller (beta) subunit of the laminin adhesion receptor, whereas no reactivity was seen with the anti-vitronectin receptor antibody. These results show that the laminin adhesion receptor is a distinct protein, one subunit of which may be related to the fibronectin receptor beta subunit. The α subunit of the laminin receptors was reactive with an antibody against a peptide modelled after the known sequence of the cytoplasmic domain of the $\alpha_3$ subunit (Hynes et al., J. Cell Biol., in press), suggesting that the α subunit of the laminin receptor is $\alpha_3$. As shown in FIG. 3, the β subunit is closely related to the fibronectin receptor β subunit. However, FIG. 4 shows that it can differ from it immunologically, at least in the case of the RuGli cell receptors.

The ligand binding specificity of the laminin receptor was studied in liposome binding assays. The receptor was incorporated into phosphatidylcholine liposome membranes by the method of Pytela et al. Cell 40:191, (1985), which is incorporated herein by reference. Briefly, a detergent solution containing the receptor and a phospholipid are dialyzed against a detergent-free buffer. The resulting liposomes adhered strongly to substrates coated with laminin. They also bound, to a variable extent, to fibronectin and type IV and type I collagen, but not to substrates coated with vitronectin, fibrinogen or albumin. In contrast, liposomes made with fibronectin receptor from the same cells bound strongly to fibronectin and showed no interaction with laminin. The attachment of the liposomes prepared with the laminin adhesion receptor was inhibited by purified cell-attachment promoting laminin fragments, but not by the GRGDSP peptide that inhibits the binding of cells to fibronectin and vitronectin (Gehlsen et al. J. Cell. Biol. 106:925–950 (1988), which is incorporated herein by reference) nor another peptide derived from laminin, YIGSR (Graf et al., Cell 48:989, (1987), which is incorporated herein by reference). All peptides are identified by their conventional one letter abbreviation. These results show that the laminin adhesion receptor can incorporate into the liposome membranes and that it conveys to liposomes the expected binding to laminin.

The laminin adhesion receptor liposomes are useful for targeting liposomes into basement membranes. For instance, deposits in the kidney glomeruli may be treated with liposomes loaded with proteolytic and other enzymes by using receptor-mediated targeting.

To coat a nonlipid surface with receptors, a receptor from a solution is adsorbed or covalently coupled to a surface such as plastic using one of the many well known methods available for such coated or coupling. Receptor fragments that retain the ligand-binding activity but lack the membrane embedded portion of the molecule are advantageously used as they are more soluble than the complete receptor. Such materials coated with receptors are useful as prostheses where attachment of basement membrane is desired, such as, for example, an artificial lens.

Figure 6:
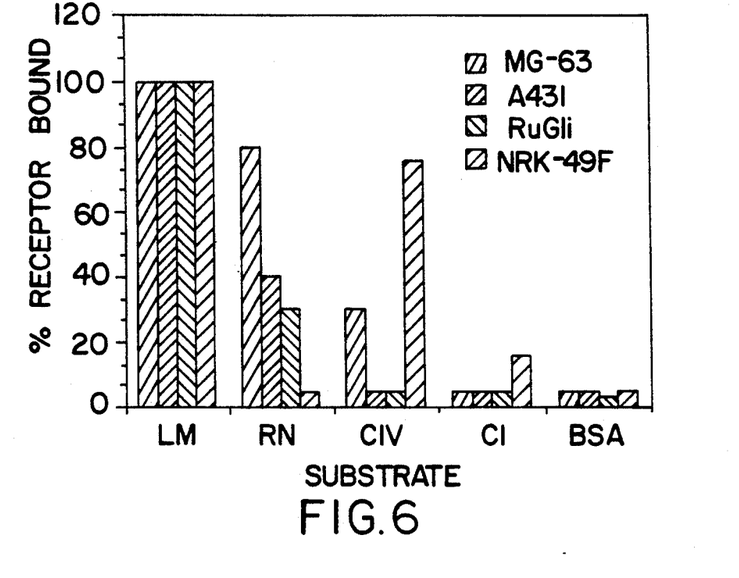

The binding specificities of the isolated laminin receptors have also been examined in a radioreceptor assay that consists of incubating $^{125}$-I labeled receptor in microtiter wells coated with laminin or other proteins and the measurement of the binding of radioactivity to the wells. The laminin receptors from each of the cell types bound to wells coated with laminin. They all showed also some affinity for fibronectin and some of the receptors bound to type IV collagen (FIG. 6). The latter result suggests that the receptors isolated from the various cell types fall into two categories—type IV collagen nonbinding (for example, RuGli) and type IV collagen binding (for example, MG63). No chemical difference has been established between these types of receptors as yet.

Figure 7:
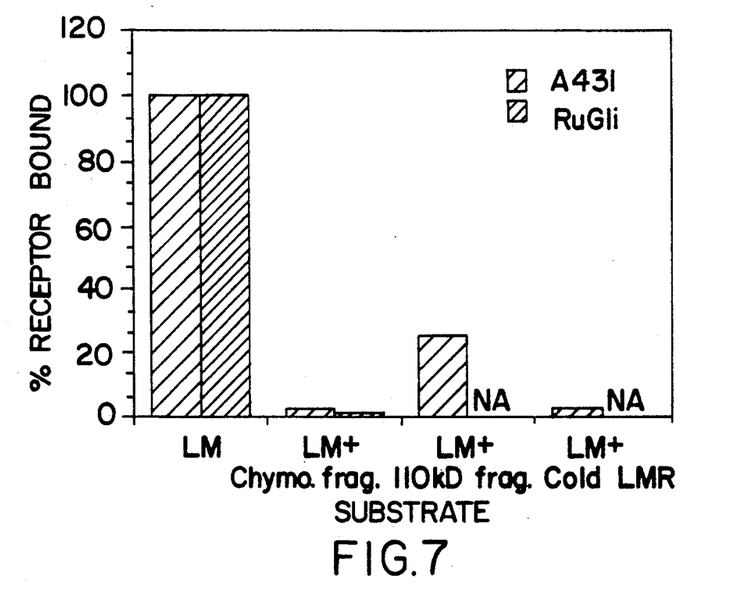
FIG. 7. Inhibition of laminin receptor binding in the radio-receptor binding assay. Data represent the percentage of laminin receptor bound to laminin-coated microtiter wells in the presence of various inhibitors compared to uninhibited laminin binding which was taken as 100 percent. Laminin receptors from A-431 cells (sparsely striped bars) and the RuGli cells (densely striped bars) were used. The inhibitors tested were laminin and fibronectin fragments and unlabeled receptor (described under Example VIII). The RuGli receptor was not tested with two of the inhibitors (NA).

The radioreceptor assay was also used to assess the ability of various protein fragments to inhibit the interaction between laminin and its receptor (FIG. 7). Fragments of laminin derived from the portion made up of the COOH-terminal parts of the molecule (Dillner et al., Exp. Cell. Res. 177:186 (1988) inhibited the binding. Moreover, fibronectin fragments derived from the cell attachment region of that molecule were also inhibitory. The ability of the fragments to inhibit the laminin receptor interaction will be useful in preventing the attachment of tumor cells to blood vessel basement membranes. The assay will be useful in identifying other substances capable of inhibiting the laminin receptor-laminin interaction.

Monoclonal and polyclonal antibodies against the laminin adhesion receptor were prepared according to procedures well known in the art. The polyclonal antibodies are absorbed with the purified fibronectin receptor coupled to Sepharose TM (Argraves et al., supra). Since the beta subunits of the laminin and fibronectin receptors are similar and since the fibronectin receptor beta subunit is shared by a number of other integrins, this treatment will eliminate antibodies directed against determinants shared by the receptors in this integrin family. It will also eliminate antibodies against contaminating proteins that would bind nonspecifically to both the laminin and fibronectin affinity matrices. If necessary, such antibodies can also be removed by absorbing the antiserum with "a mock-purified receptor preparation" (see Example VI). The specificity of the antibodies is examined by carrying out enzyme immunoassays, immunoprecipitation of detergent extracts from surface-iodinated and metabolically labeled cells and immunoblotting of isolated laminin receptor, other isolated integrins and whole cell extracts by methods well known in the art. As shown in FIG. 4, in the case of the RuGli cell receptors, the absorption of an antiserum made against the RuGli cell laminin receptor with the RuGli cell fibronectin receptor yielded an antibody preparation that is primarily reactive with the laminin receptor.

Monoclonal antibodies are prepared by immunizing with the isolated receptor or other material containing the receptor followed by isolation of antibody-producing hybridoma cells, as is well known in the art. (See, for example, Harlow and Lane, ANTIBODIES: A LABORATORY MANUAL, Cold Spring Harbor, 1988, which is incorporated herein by reference.) The appropriate hybridoma cells are selected by performing enzyme immunoassays with the purified laminin receptor. Antibodies specific for the laminin receptor are obtained by using immunoblotting to select those antibodies that are reactive with either one of the subunits of the laminin receptor but do no react with other integrin subunits. To obtain antibodies specific for the laminin receptor that can inhibit the laminin-binding activity of the receptor, the subunit-specific monoclonal antibodies are tested as inhibitors of cell attachment to laminin. This assay is performed by allowing cells to attach to microtiter wells in the presence and absence of the antibody. Finally, selection of antibodies that promote attachment is performed by coating microtiter wells with purified antibody at various concentrations followed by addition of cells possessing the laminin receptor into the wells. Increased attachment of the cells relative to wells coated with an inert protein such as serum albumin shows the presence of antibody with the desired properties.

The laminin adhesion receptor can also be used to screen various compounds for their ability to compete for binding to laminin. Preferably, such screening is accomplished using an inhibition assay, such as that described in Example VIII, although other methods will be obvious to one skilled in the art. The inhibition assay can be used advantageously to screen unknown substances or mixtures of substances for inhibitory activity. If such a mixture is found to have inhibitory activity, it can then be fractionated in order to isolate or identify the particular active compound. Such active compounds can then be used either to promote attachment to a substrate of cells exhibiting laminin adhesion receptors by coating the substrate with such a compound or to inhibit adhesion of such cells to laminin by providing the compound in soluble form.

The following examples are intended to illustrate but not limit the invention. While they are typical of those that might be used, other procedures known to those skilled in the art may be alternatively employed.

EXAMPLE I

ISOLATION OF LAMININ RECEPTOR a. RuGli Cells

Glioblastoma cell line RuGli, obtained from the Max Planck Institute, Tubigen, West Germany, was used as a source of rat laminin adhesion receptor. Cells were grown to confluency and the cell surfaces were iodinated with $^{125}I$ by the lactoperoxidase method (Lebien et al, J. Immunol. 129:2287 (1982), which is incorporated herein by reference) and extracted with Tris-buffered saline, pH 7.2, containing 25 mM octyl-beta-D-thioglucoside (Calbiochem, La Jolla, Calif.), 1 mM $MnCl_2$, and 1 mM phenylmethylsulfonylfluoride (PMSF) (extraction buffer). $Mn^{2+}$ was included in the buffer because it facilitates the isolation of the fibronectin receptor by fibronectin affinity chromatography.

Laminin fragments having cell attachment promoting and neurite promoting activity were isolated from human placenta by the immunoaffinity chromatography method of Wewer et al., J. Biol. Chem. 258:12654 (1983), which is incorporated herein by reference. The 4E10 anti-human laminin antibody that was used for isolation is commercially available from Telios Pharmaceuticals, Inc., San Diego, Calif.

A laminin-Sepharose TM column was prepared by coupling 90 mg of human laminin fragments, obtained as above, to 10 ml of cyanogen bromide-activated Sepharose TM gel (Pharmacia, Uppsala, Sweden) following the manufacturer's instructions.

The soluble extract from 5 ml of packed surface-iodinated cells was applied to a 10 ml (bed volume) laminin-Sepharose column. The cell extract was passed through the column two times and the column was washed with 30 ml of the extraction buffer. An initial dilution was done with 20 ml buffer containing 2 mg/ml of the synthetic peptide GRGDSP followed by 20 ml of cation-free buffer containing 20 mM EDTA. Aliquots of each collected 2 ml fraction were electrophoresed on a 7.5% SDS polyacrylamide gel under non-reducing conditions. Protein bands were visualized by overnight autoradiography. The GRGDSP elution released no specifically eluted bands from the affinity matrix, whereas the EDTA elution released a laminin adhesion receptor as shown in FIG. 1.

As shown in FIGS. 1 and 2, in the incompletely unfolded state in which the protein derived from RuGli cells exists under non-reducing conditions, two protein bands migrating at positions corresponding to the apparent molecular weights of 150 kD and 120 kD were seen. A more accurate molecular weight determined by SDS-PAGE under reducing conditions indicates the molecular weights of these subunits are about 165 and 140 kD, respectively, because, when reduced, the larger of the subunits gives rise to two polypeptides, 135 kD band and a 35/30 kD doublet. While not wishing to be bound by this explanation, it is believed that the 30 kD polypeptide is a cleavage fragment of the 35 kD polypeptide.

b. MG-63, A-431, and U-251 Cells

Human osteosarcoma cells (MG-63; ATCC Accession No. CRL 1427) human epidermal carcinoma cells (A-431; ATCC Accession No. CRL-1555) and human glioblastoma cells (U-251) were used as sources of human integrin-type laminin receptors. The receptors were isolated by the methods described above for the RuGli receptor. The receptor obtained had the same electrophoretic appearance as the RuGli receptor shown in FIG. 1, except that the larger ($\alpha$) subunit migrated somewhat more slowly than the RuGli receptor $\alpha$ subunit giving an apparent molecular weight of about 170,000 D.

EXAMPLE II

INCORPORATION OF LAMININ RECEPTOR INTO LIPOSOMES AND BINDING OF THE LIPOSOMES TO SUBSTRATES

Phosphatidylcholine liposomes incorporating the cell surface receptors were prepared essentially by the method of Mimms et al., Biochemistry 20:883, (1981), as described for the fibronectin receptor (Pytela et al., Meth. Enzymol. 144:475-489, 1987), both references being incorporated herein by reference. Egg yolk phosphatidylcholine (Sigma, St. Louis, Mo.) and $^3$H-phosphatidylcholine (New England Nuclear, Boston, Mass.), were dissolved in the receptor fractions at 100 $\mu$g/ml and this solution was then dialyzed against 50 mM Tris-HCl containing 500 mM NaCl, 1 mM Ca$_2$Cl and 1 mM Mg$_2$Cl for 24 hours at 4° C. The resulting liposomes were isolated by floating to the surface of a sucrose gradient in ultracentrifugation and tested for binding of various substrates.

Figure 5:
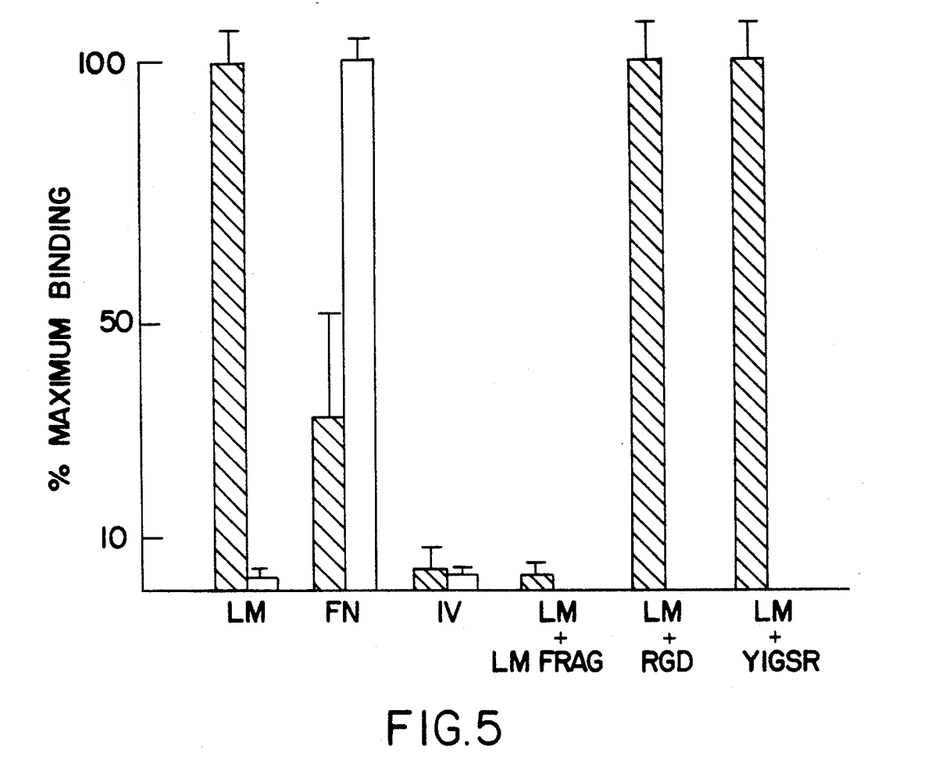

The substrates were prepared by coating polystyrene microtiter plate wells (Linbro/Titertek, Inglewood, Calif.) with extracellular matrix proteins including laminin, fibronectin, collagens and vitronectin (Telios Pharmaceuticals, Inc., La Jolla, Calif.), according to the method of Engvall et al., J. Cell. Biol. 103:2457 (1986), which is incorporated herein by reference, using 20 $\mu$g/mL in PBS overnight at 4° C. Coating with bovine serum albumin (BSA; 5 mg/mL) was used to determine nonspecific background binding (Sigma Chemical Co., St. Louis, Mo.). The laminin receptor-liposome preparations showed strong dose-dependent binding to microtiter wells coated with laminin, bound slightly to fibronectin, and showed no binding over the background to collagens type I or IV or to vitronectin, as shown in FIG. 5.

The fibronectin receptor isolated from the same RuGli cell extract was used for comparison in the liposome assay. Liposomes prepared with this receptor bound to a greater degree to fibronectin than the laminin receptor liposomes and showed no binding to laminin. Further specificity controls included inhibition of the laminin receptor binding by adding cell attachment-promoting chymotryptic human laminin fragments to the liposome assay. These fragments inhibited the binding of the laminin receptor liposomes to laminin, whereas the GRGDSP peptide or the YIGSR laminin peptide did not. Representative results from these assays are shown in FIG. 5.

EXAMPLE III

USE OF THE RECEPTOR-LIPOSOME PREPARATION TO TARGET THERAPEUTIC AGENTS

Receptor liposomes are prepared as described above and a desired therapeutic agent is incorporated into them according to published methods (Gregoriadis and Senior, Biochem. Soc. Trans. 12:337, (1984) which is incorporated herein by reference). These conjugated liposomes are injected intravenously using 1-300 $\mu$mol of lipid per kg of body weight or applied locally. Such laminin receptor liposomes are used for example, to target drugs to tissues that contain large amounts of laminin.

EXAMPLE IV

ANALYSIS OF RECEPTOR SPECIFICITY BY RADIORECEPTOR ASSAY

The binding of laminin receptor to laminin and the effect of antibodies and protein fragments on this binding was examined in a radio-receptor assay previously described for the fibronectin receptor (Hautanen, et al., J. Biol. Chem. 264:1437-1442 (1989)). Microtiter wells were coated with 1-2 $\mu$g/ml of human laminin, bovine type I collagen (Collaborative Research, Lexington, Mass.), mouse type IV collagen (BRL, Bethesda, Md.), human plasma fibronectin or bovine serum albumin. $^{125}$I-labeled receptor isolated from surface iodinated cells was allowed to bind to the coated wells for 2 hours at room temperature in the presence of Tris-buffered saline (150 mM NaCl, 50 mM Tris-HCl, pH 7.5, TBS) containing 50 mM octyl-$\beta$-glucopyranoside, 1 mM PMSF, and 1 mM MnCl$_2$. The amount of receptor added per well was equivalent to $10^4$ cpm. Following incubation, wells were washed, and bound receptor was solubilized with 1% sodium dodecyl sulfate (SDS) in TBS, and quantitated by counting the bound radioactivity. Nonspecific binding was measured in wells coated with albumin. The total binding varied between 5 and 10% of the added radioactivity, and 70-80% of this was specific by the above criteria. The laminin receptors from each of the cell types tested bound to laminin in the assay as shown in FIG. 6. The receptors also bound to varying degrees to fibronectin and type IV collagen. The reasons for this variation are not known. Without wishing to be bound by that explanation, it is believed that the difference may be in the $\beta$ subunit of the receptor such that the receptor with affinity for type IV collagen has the composition $\alpha_3\beta_1$, (See Ruoslahti and Pierschbacher, supra) and the one with no affinity for type IV collagen has a different $\beta$ subunit. Support for this position is provided by the immunological differences between the RuGli cell laminin and fibronectin receptors documented in FIG. 4.

EXAMPLE V

LOCALIZATION OF THE LAMININ RECEPTOR BINDING SITE a. Electron Microscopy

Electron microscopic analysis of laminin receptor-laminin complexes was performed as described for receptor-fibronectin complexes (Gailit and Ruoslahti, J. Biol. Chem. 263:12927 (1988), Which is incorporated herein by reference) with some modifications. Receptor preparations from affinity chromatography eluates were mixed with either mouse laminin (BRL, Bethesda, Md). or with pepsin fragments of human laminin (Dillner, et al., Exp. Cell. Res. 177:186 (1988), which is incorporated herein by reference) in the presence of 1 mM each of $Ca^{2+}$, $Mg^{2+}$ and $Mn^{2+}$. Various ratios of receptor and laminin were used, and all incubations of the receptor-laminin complexes were performed at 4° C. to avoid the aggregation of laminin known to take place in the presence of divalent cations at higher temperatures.

When the laminin receptors were mixed with mouse laminin, some of the laminin molecules appeared to have complexed with the receptor. The receptor was bound to the globular end of the laminin long arm in these complexes. No structures resembling the laminin receptor complexes were observed in control preparations consisting of laminin alone or laminin mixed with the MG-63 or RuGli cell fibronectin receptor. Examination of a large number of fields from several independently prepared samples showed that among more than 100 possible receptor-laminin complexes, approximately 80% had the receptor associated with the globular domain at the end of the long arm. Among the remainder of the possible complexes, the receptor molecule appeared to be associated variously with one of the short arms or the center of the cross. Laminin-receptor complexes similar to those obtained with mouse laminin were seen when pepsin fragments of human laminin were mixed with the laminin receptor.

b. Localization with Monoclonal Antibodies

The preferential binding of the receptor to the globular domain at the end of the long arm of the laminin molecule was similar to what has previously been shown for a group of monoclonal antibodies capable of inhibiting the neuritepromoting activity of laminin. Monoclonal antibodies against pepsin-extracted human laminin were prepared by the method of Engvall et al., J. Cell Biol. 103:2457-2465 (1986), which is incorporated herein by reference. The ability of two of these antibodies, 3E5 and 4E10, to interfere with the binding of the receptor to laminin in a radio-receptor assay was examined. The 3E5 and 4E10 antibodies inhibited the binding of the RuGli receptor to laminin in a concentration-dependent fashion. Antibody 2E8, which has no effect on neurite outgrowth and which binds to a region near the center of the laminin cross, showed little inhibition at comparable antibody concentrations. A monoclonal antibody of unrelated specificity was also ineffective. The binding of the MG-63 cell receptor was similarly inhibited by the 3E5 and 4E10 antibodies in this assay, indicating that both laminin receptors may bind to the same site.

c. Localization of monoclonal antibody binding site by cDNA cloning

Laminin cDNA clones were isolated to test proteins produced by these clones for the binding of the monoclonal antibodies that defined the receptor binding site. Screening of placental and endothelial cell gt11 cDNA libraries with polyclonal and monoclonal antibodies to laminin yielded numerous reactive clones. DNA sequencing and comparison to the previously published laminin sequences (Pikkarainen, et al., J. Biol. Chem. 262:10454-10462 (1987) and Pikkarainen, et al., J. Biol. Chem. 263:6751-6758 (1988)) showed that several of these clones coded for COOH-terminal portions of the B1 and B2 chains. No A chain clones were identified.

Fusion proteins expressed from the B1 and B2 chain clones were tested for reactivity with the monoclonal antibodies in macroplaque filter assay (Suzuki, et al., EMBO J. 4:2519-2524 (1985)). The fusion proteins from all clones encoding the COOH-terminus of the B1 chain reacted with the 3E5 antibody, whereas this antibody did not react with the B2 chain fusion proteins. The shortest clone reactive with the 3E5 antibody encodes the 252 COOH-terminal amino acids of the B1 chain. None of the fusion proteins from the COOH-termini of the B1 and B2 chains, were reactive with the other antibody 4E10.

EXAMPLE VI

PREPARATION OF ANTIBODIES TO LAMININ RECEPTOR AND THEIR USE TO DETECT THE RECEPTOR a. Polyclonal antibodies

Rabbits were immunized with purified laminin receptor in Freund's complete adjuvant. Booster injections containing 50 μg of receptor in Freund's incomplete adjuvant were given at three week intervals and serum is collected one week after the last injection. The antiserum was absorbed with human plasma-proteins, fibronectin and laminin, each coupled to Sepharose TM. In addition, absorption with a "mock-purified receptor" that was obtained by fractionating the same cell or tissue extract that served as the source of the laminin receptor on a Sepharose TM column to which bovine serum albumin was coupled. The same procedure as in the receptor isolation was followed and those fractions that in the receptor isolation contained the receptor were collected as the mock purified receptor. The antiserum was then further absorbed with fibronectin receptor, also coupled to Sepharose TM. The fibronectin receptor was isolated by the method of Pytela et al., Supra. The absorption with the mock purified receptor-Sepharose and fibronectin receptor-Sepharose TM was carried out by passing 2 ml of serum sequentially through columns of 1 ml Sepharose containing 100 μg of the mock-purified receptor proteins or 100 μg of the fibronectin receptor. The nonbound material was tested for its reactivity by solid phase enzyme immunoassay (ELISA; Engvall, Meth. Enzymol. 70:419-439, 1980 which is incorporated herein by reference) with the purified laminin receptor and fibronectin receptor as antigens, and by SDS-PAGE immunoblotting against the receptors and against a whole cell extract or tissue extract from the cells or tissue that served as the source of the receptor. The absorptions were repeated until these assays showed that the antiserum is specific. The antiserum was considered specific for the laminin receptor when it reacted only with the laminin receptor in ELISA, and bound only to the laminin receptor subunits but not to the fibronectin receptor subunits in immunoblotting, performed according to the method of Towbin et al., Proc. Natl. Acad. Sci. USA 76:4350 (1979) and Argraves et al, supra, (see FIG. 4), which is incorporated herein by reference. The same procedure was used to obtain fibronectin receptor specific antibodies from the fibronectin receptor antiserum by absorption with the mockpurified receptor proteins and the laminin receptor. The receptor-Sepharose TM columns were regenerated by washing with 8 M urea in 50 mM Tris-HCl, pH 7.0.

b. Monoclonal antibodies

Mice were immunized with 10 $\mu$g of purified laminin receptor per injection with the first injection given subcutaneously in Freund's complete adjuvant and the booster injection intraperitoneally without adjuvant. Spleen cells from the immunized mice were collected 3 days after the booster injection and used to generate hybridomas as described in the literature. Hybridomas secreting antibody that reacts with the laminin receptor were selected by solid phase enzyme immunoassay with the laminin receptor as the antigen (Engvall, et al., Meth. Enzymol. 70:419-439, 1980). For the assay, microtiter wells were coated with 1 $\mu$g/ml of receptor solution diluted from the octylglucoside-containing stock solution at least 1:10 to phosphate-buffered saline. Those antibodies that were specifically reactive with the laminin receptor were further selected by testing the positive antibodies against the fibronectin receptor. This reactivity was verified for those antibodies that were reactive with the SDS-denatured receptor by SDS-PAGE immunoblotting against cell extracts containing receptors other than the laminin receptor.

Further selection of antibodies that inhibit the laminin-binding function of the receptor was carried out in cell attachment assays. The monoclonal antibodies were isolated from the hybridoma culture media by affinity chromatography on protein A-Sepharose TM (Pharmacia, Uppsala, Sweden), although other methods well known in the art can be used and the isolated antibody was tested for its ability to inhibit the attachment of cells that served as the source of the immunizing receptor to laminin. Microtiter wells were coated with 1 $\mu$g/ml of cell attachment-promoting human laminin fragments and the RuGli cells were added to the wells with various concentrations of each monoclonal antibody. Polyclonal anti-laminin receptor antibodies were used as a positive control and anti-fibronectin receptor alpha subunit monoclonal antibodies as a negative control. Fewer cells were attached to the wells at the end of the assay when the antibody had the desired inhibitory activity.

EXAMPLE VII

TESTING OF ANTI-LAMININ RECEPTOR ANTIBODIES IN TUMOR INVASION ASSAYS

To test for the ability of anti-laminin alpha subunit antibodies to interfere with the invasion of tumor cells through tissue, an amniotic membrane invasion assay is used. RuGli glioblastoma cells are allowed to migrate through an amniotic membrane as described in the literature (Gehlsen et al., J. Cell Biol. 106:925-930, 1988 which is incorporated herein by reference) in the presence of various concentrations of the anti-laminin receptor antibodies and the same control antibodies described above. Fewer cells will migrate through the amniotic membrane in the presence of inhibitory antibodies than in the controls.

EXAMPLE VIII

INHIBITION OF LAMININ RECEPTOR IN THE RADIO-RECEPTOR BINDING ASSAY

Microtiter wells were coated with laminin at 1 to 2 $\mu$L in PBS as described in Example IV. Laminin receptor isolated from A-431 or RuGli cells as described in Example I was then added to the microtiter wells either alone (LM) or in the presence of chymotrypsin fragments of laminin (chymo. frag., 25 $\mu$g/mL Dillner, et al., Supra), the 110 kD fragment of fibronectin (110 kD frag., 25 $\mu$g/mL, 120 kDfragment in Pierschbacher et al., Cell 26:259-267 (1981)) or unlabelled laminin receptor (Cold LMR).

The results are shown in FIG. 7. Data represent the percentage of laminin receptor bound compared to uninhibited laminin binding at 100 percent. As can be seen, cell attachment promoting fragments of laminin derived from the portion made up of the COOH-terminal parts of the molecule inhibited the binding of the laminin receptor to the laminin coated wells. Moreover, the fibronectin fragment, which is derived from the cell attachment region of that molecule, was also inhibitory. As expected, unlabeled laminin receptor, which was tested as a control, also inhibited the binding of the radioactive receptor.

INDUSTRIAL APPLICATION

This invention finds direct and immediate application in the assay of laminin receptor in cells and tissues. The isolation method described above can be used to assay cultured cells or tissue samples for their content of the laminin receptor. Such analysis will be important in determining the adhesion capacity of cells such as those in tumors. Alternatively, the isolated receptor can be used to prepare antibodies for receptor quantitation. Together with such antibodies, the receptor will permit establishment of assays for the receptor such as a radioimmunoassay or ELISA. Compounds binding to the receptor so that they compete with the binding of the receptor to laminin can be selected with the receptor and are useful, for example, in preventing attachment of the tumor cells to basement membranes during tumor invasion. Alternatively, such substances, when presented in an insoluble form may be used to reproduce the cell attachment promoting effect of laminin in tissue reconstruction. A reagent consisting essentially of the laminin receptor described in the foregoing examples may be used to carry substances to selected tissues.

Although the invention has been described with reference to the presently-preferred embodiments, it should be understood that various modifications can be made without departing from the spirit of the invention. Accordingly, the invention is limited only by the following claims.

We claim:

1. A substantially pure active mammalian laminin adhesion receptor, characterized by comprising two subunits, one of which is $\alpha_3$, the $\alpha_3$ subunit further comprising two disulfide linked polypeptides, said receptor selectively binding with laminin or cell attachment-promoting fragments of laminin.

2. The receptor of claim 1, wherein said mammalian laminin adhesion receptor is derived from a rat.

3. The receptor of claim 1, wherein said mammalian laminin adhesion receptor is derived from a human.

4. The receptor of claim 1, wherein said receptor can be eluted from said selective binding with laminin or cell attachment-promoting fragments of laminin with ethylenediaminotetraacetic acid.

5. A composition of matter comprising the receptor of claim 1 incorporated into lipid vesicles.

6. A composition of matter comprising the receptor of claim 1 coated onto a substrate.

7. A composition of matter comprising fragments of a substantially pure active mammalian laminin adhesion receptor which retain ligand binding activity, said receptor characterized by comprising two subunits, one of which is $\alpha_3$, the $\alpha_3$ subunit further comprising two disulfide liked polypeptides, said receptor selectively binding with laminin or cell attachment-promoting fragments of laminin.

8. Laminin cell surface receptors isolated by the method comprising:
 a. running a mammalian cell extract preparation through an affinity column comprising the cell attachment-promoting portion of laminin coupled to a matrix, wherein said cell extract preparation is run through said column in the presence of divalent cation so as to achieve binding between the laminin cell surface receptors to be isolated and laminin cell attachment site;
 b. eluting said column with a solution containing a substance capable of selectively eluting said laminin cell surface receptor; and
 c. collecting said laminin cell surface receptors eluted thereby.

* * * * *

UNITED STATES PATENT AND TRADEMARK OFFICE
CERTIFICATE OF CORRECTION

PATENT NO. : 5,180,809
DATED : January 19, 1993
INVENTOR(S) : Ruoslahti et al.

It is certified that error appears in the above-identified patent and that said Letters Patent is hereby corrected as shown below:

In column 2, line 67, please delete "cell-attachmentpromoting" and insert therefore --cell-attachment-promoting--.

In column 7, line 54, please delete "do no react" and insert therefore --do not react--.

In column 12, line 7 please delete "gt11" and insert therefore --λgt11--.

In column 13, line 10, please delete "mockpurified" and insert therefore --mock-purified--.

In column 14, line 16, please delete "kDfragment" and insert therefore --kD fragment--.

In the claims, column 15, line 18, please delete "disulfide liked" and insert therefore --disulfide linked--.

Signed and Sealed this

Thirteenth Day of September, 1994

Attest:

BRUCE LEHMAN

Attesting Officer

Commissioner of Patents and Trademarks